US009034919B2

(12) United States Patent
Cherukuri et al.

(10) Patent No.: US 9,034,919 B2
(45) Date of Patent: May 19, 2015

(54) BIOACTIVE-RICH CONCENTRATES AND NUTRITIVE AND THERAPEUTIC PRODUCTS CONTAINING SAME

(75) Inventors: Aravind Cherukuri, Newton, MA (US); Reddy Sastry V. Cherukuri, Folsom, CA (US); Rukmini C. Cherukuri, Folsom, CA (US); Kartik Natarajan, West Hartford, CT (US)

(73) Assignee: Kartik Natarajan, West Hartford, CT (US)

( * ) Notice: Subject to any disclaimer, the term of this patent is extended or adjusted under 35 U.S.C. 154(b) by 1312 days.

(21) Appl. No.: 11/406,068

(22) Filed: Apr. 18, 2006

(65) Prior Publication Data

US 2007/0243233 A1  Oct. 18, 2007

(51) Int. Cl.

| C07D 311/72 | (2006.01) |
| A61K 35/00 | (2006.01) |
| A61K 36/00 | (2006.01) |
| A23L 1/30 | (2006.01) |
| A61K 31/22 | (2006.01) |
| A61K 31/366 | (2006.01) |
| A61K 31/401 | (2006.01) |
| A61K 31/56 | (2006.01) |
| A61K 45/06 | (2006.01) |
| A61K 36/899 | (2006.01) |
| A23L 1/164 | (2006.01) |

(52) U.S. Cl.
CPC .............. *A61K 36/899* (2013.01); *A61K 35/00* (2013.01); *A61K 36/00* (2013.01); *C07D 311/72* (2013.01); *A23L 1/164* (2013.01); *A23L 1/1643* (2013.01); *A23L 1/3004* (2013.01); *A61K 31/22* (2013.01); *A61K 31/366* (2013.01); *A61K 31/401* (2013.01); *A61K 31/56* (2013.01); *A61K 45/06* (2013.01)

(58) Field of Classification Search
CPC ....... C07D 311/72; A61K 35/00; A61K 36/00
See application file for complete search history.

(56) References Cited

U.S. PATENT DOCUMENTS

| 5,288,902 | A |   | 2/1994  | Taniguchi et al. |
| 5,290,579 | A |   | 3/1994  | Hitotsumatsu et al. |
| 5,514,398 | A | * | 5/1996  | Imai et al. ............... 426/271 |
| 5,552,167 | A | * | 9/1996  | Taylor et al. ............ 426/99 |
| 5,660,691 | A |   | 8/1997  | Barnicki et al. |
| 5,985,344 | A |   | 11/1999 | Cherukuri et al. |
| 6,126,943 | A |   | 10/2000 | Cheruvanky et al. |
| 6,197,357 | B1|   | 3/2001  | Lawton et al. |
| 6,303,586 | B1|   | 10/2001 | McPeak et al. |
| 6,350,473 | B1|   | 2/2002  | Cheruvanky et al. |
| 6,558,714 | B2|   | 5/2003  | Cheruvanky et al. |
| 6,733,799 | B2|   | 5/2004  | Cheruvanky et al. |
| 2005/0053712 | A1 |   | 3/2005  | Zima et al. |
| 2005/0054866 | A1 |   | 3/2005  | Rohr et al. |
| 2006/0083700 | A1 |   | 4/2006  | Cherukuri et al. |
| 2009/0155396 | A1 |   | 6/2009  | Cherukuri et al. |

FOREIGN PATENT DOCUMENTS

| EP | 2012598 A1 | 1/2009 |
| IN | 6081/CHENO/2008 | 11/2008 |
| JP | 2005255563 | 9/2005 |
| JP | 2005255746 | 9/2005 |
| WO | WO-9910002 | 3/1999 |
| WO | WO-9911144 | 3/1999 |
| WO | WO 9963031 A1 * | 12/1999 |
| WO | WO-02060272 | 8/2002 |
| WO | WO 2007-120144 A1 | 10/2007 |

OTHER PUBLICATIONS

Sharma, R.D. and Rukmini C. (1987) "Hypocholesterolemic Activity of of Unsaponifiable Matter of Rice Bran Oil" *Indian Journal of Medical Research.* 85: 278-281.

Joo-Shin Kim et al., (2001) "Inhibition of Cholesterol Autoxidation by the Nonsaponifiable Fraction in Rice Bran in an Aqueous Model System" *Journal of the American Oil Chemists*, 78(7): 685-689.

Nicolosi R J et al., "Nutrient Bar Reduces Cholesterol Levels" *Food Technology* (1996) 50(3): 93.

Akihisa, Toshihiro, et al., "Triterpene Alcohol and Sterol Ferulates from Rice Bran and Their Anti-inflammatory Effects" *J. Agri. Food Chem.* 2000, 48, 2313-2319.

Ausman, Lynne M. et al., "Hypocholesterolemic Effect of Physically Refined Rice Bran Oil: Studies of Cholesterol Metabolism and Early Atherosclerosis in Hypercholesterolemic Hamsters" *Journal of Nutritional Biochemistry* 16 (2005) 521-529.

Berger, Alvin, et al., "Similar Cholesterol-lowering Properties of Rice Bran Oil, with Varied γ-Oryzanol, in Mildly Hypercholesterolemic Men" *Eur J. Nutr* (2005) 44:163-173.

Bouic P. J. D., Etsbeth S., Liebenberg R.W., Albrecht C. F, Pegel G., Van Jaarsveld P.P. (1996) "Beta-sitosterol and beta-sitosterol glucoside stimulate human peripheral blood lymphocyte proliferation: Implication for their use as an immunomodulatory vitamin combination", *International. J. Immunopharmacology*, 18(12): 693-700.

Bruni, Joseph, "The facts on γ-oryzanol" 1987.

Cheruvanky, Rukmini (2000) In "Phytochemicals as Bioactive Agents." Bidlack, W. R., Omaye, S. T., Meskin, M. S., Topham, D. K. W (Ed), Chapter 13 "Bioactives in Rice Bran and Rice Bran Oil." 213-239.

Cheruvanky, R., and Raghuram T.C. (1991) "Nutritional and biochemical aspects of the hypolipidemic action of rice bran oil: A review" *J. Amer. Coll. Nutrition.* 10: 593-601.

Cicero, A.F. and Gaddi, A. (2001) "Rice bran oil and gamma oryzanol in the treatment of Hyperlipoprotenaemias and other conditions" *Phytotherapy.* Res, 15-277-289.

de Deckere, E.A.M. et al., (1996) "Minor Constituents of Rice Bran Oil as Functional Foods" *Nutrition Reviews*, vol. 54, No. 11, p. S120-S126.

Fan, Q. et al., "Nutritional Evaluation of Rice Bran Oil and a Blend with Corn Oil" *Die Nahrung* 39 (1995) 5/6, 490-496.

(Continued)

*Primary Examiner* — Sarah Pihonak

(57) ABSTRACT

This invention relates generally to the field of compositions for use as nutraceuticals, food additives or adjuncts to conventional drug therapies. In particular, the invention relates to compositions derived from natural oil sources which can be used for effective and inexpensive treatment of cardiovascular diseases, hypercholesterolemia, diabetes, cerebrovascular disease, neurological disorders, or liver abnormalities.

19 Claims, 5 Drawing Sheets

(56) References Cited

OTHER PUBLICATIONS

Frank, N. et al., "Effects of Rice Bran Oil on Plasma Lipid Concentrations, Lipoprotein Composition, and Glucose Dynamics in Mares" *Journal of Animal Science*, 2005, 83:2509-2518.

Ha, Tae-Youl, et al., (2005) "Bioactive Components in Rice Bran Oil Improve Lipid Profiles in Rats Fed a High-Cholesterol Diet" *Nutrition Research* 25: 597-606.

Hegsted, Maren, et al., "Rice Bran and Rice Bran Oil May Lower Heart Disease Risk by Decreasing Cholesterol Synthesis in the Body" *Louisiana Agriculture*, vol. 37, No. 2, Spring 1994, p. 16-17.

Hudson, E. Ann, et al., "Characterization of Potentially Chemopreventive Phenols in Extracts of Brown Rice That Inhibit the Growth of Human Breast and Colon Cancer Cells" *Cancer Epidemiology, Biomarkers & Prevention*, vol. 9, Nov. 2000, p. 1163-1170.

Jariwalla, R.J. "Rice-Bran Products: Phytonutrients with Potential Applications in Preventive and Clinical Medicine" *Drugs Exp Clin Res.* 27(1) 17-26 (2001).

Juliano, Claudia, et al., "Antioxidant Activity of Gamma-Oryzanol: Mechanism of Action and Its Effect on Oxidative Stability of Pharmaceutical Oils" *International Journal of Pharmaceutics*, 299 (2005) 146-154.

Lee, J., Lee, S., Kim,. M., Rhee, C., Kim, I., and Lee, K (2005) "Beneficial effect of the unsaponifiable matter from from rice bran on oxidative stress in vitro compared with alpha tocopherol" *J. Sci. Food. Agric.*, 85: 493-498.

Lichtenstein, A.H, et al. (1994) "Rice bran oil consumption and plasma lipid levels in moderately hypercholesterolemic humans" *Arteriosclerosis and Thrombosis*, vol. 14, 549-556.

Minhajuddin, M., Beg, Z.H. and Iqbal, J. (2005) "Hypolipidemic and antioxidant properties of tocotrienol rich fraction isolated from rice bran oil in experimentally induced hyperlipidemic rats" *Food and Chemical Toxicology* 43(5): 747-753.

Most, Marlene M. et al., "Rice Bran Oil, Not Fiber, Lowers Cholesterol in Humans" *Am J. Clin Nutr* 2005; 81: 64-68.

Murray, Frank, "High Cholesterol? Reduce Your Risk with Rice Bran Oil Extract" *Let's Live*, May 1997, 63-65.

Nesaretnam, Kalanithi, et al., "Tocotrienols Inhibit the Growth of Human Breast Cancer Cells Irrespective of Estrogen Receptor Status" *Lipids*, vol. 33, No. 5 (1998) 461-469.

Nicolosi R.J., Ausman L.M., and Hegstead M. (1991) "Rice bran oil lowers serum total and low density lipoprotein cholesterol and apo B levels in nonhuman primates" *Atherosclerosis*. 88(2-3) 133-142.

Normén L, et al., "Combination of Phytosterols and Omega-3 Fatty Acids: A Potential Strategy to Promote Cardiovascular Health" *Curr. Med. Chem.—Cardiovascular & Hematological Agents*, 2004, 2, 1-12.

Orthoefer, Frank T. "Rice Bran Oil: Healthy Lipid Source" *Food Technology*—Dec. 1996, vol. 50(12) 62-64.

Polasa,K. and Rukmini,C. "Ames mutagenicity test of deep fat fried foods prepared using rice bran oils as frying medium" *J Oil Tech Assoc India* 19 (1987) 15.

Purushothama, S. et al., "Effect of Long Term Feeding of Rice Bran Oil Upon Lipids and Lipoproteins in Rats" *Molecular and Cellular Biochemistry* 146: 63-69, 1995.

Qureshi, Asaf A. et al., (2000) "Isolation and Identification of Novel Tocotrienols from Rice Bran with Hypocholesterolemic, Antioxidant, and Antitumor Properties" *Journal of Agricultural and Food Chemistry*, vol. 48, No. 8, 3130-3140.

Qureshi, Asaf A. et al., "Lowering of Serum Cholesterol in Hypercholesterolemic Humans by Tocotrienols (Palmvitee)" *Am J Clin Nutr* 1991; 53:1021S-1026S.

Qureshi, Asaf A. et al., "Novel Tocotrienols of Rice Bran Inhibit Atherosclerotic Lesions in C57BL/6 ApoE-Deficient Mice" 2001 *American Society for Nutritional Sciences*. 2606-2618.

Qureshi A.A., Bradlow B. A., Salser W. A., Brace L. D. (1997) "Novel tocotrienols of rice bran modulate cardiovascular disease risk parameters of hypercholesterolemic humans" *J. Nutr. Biochem* 8: 290-298.

Qureshi, A.A. et al., "Response of Hypercholesterolemic Subjects to Administration of Tocotrienols" *Lipids*, vol. 30, No. 12 (1995) 1171-1177.

Raghuram, T.C. et al., (1989) "Studies on hypolipidemic effects of dietary Rice Bran Oils in humans" *Nutrition Reports International* 39(5):889-895.

Rong, N., Ausman, L. M., Nicolosi, R.J. (1997) "Oryzanol decreases cholesterol absorption and aortic fatty streaks in hamsters" *Lipids* 32(3): 303-309.

Rukmini, C. "Chemical, Nutritional and Toxicological Studies of Rice Bran Oil" *Food Chemistry* 30 (1988) 257-268.

Rukmini, C. (2003) "Phytochemical Products: rice bran" Chapter 17, p. 347-376; in "Phytochemical Functional Foods" (Ed) Ian Johnson and Gary Williamson (CRC) Woodhead Publishing Ltd. (Great Briton).

Rukmini, C. et al., "Serum Lipid of Healthy Human Subjects on Diets Enriched with oils like Safflower/Sunflower/Safflower-Rice Bran and Sunflower-Rice Bran Blends" National Institute of Nutrition, Indian Council of Medical Research.

Seetharamaiah, G.S. et al., "Studies on Hypocholesterolemic Activity of Rice Bran Oil" *Atherosclerosis*, 78 (1989) 219-223.

Sen, Chandan K. et al., "Tocotrienol, The Natural Vitamin E to Defend the Nervous System?" *Ann. N.Y. Acad. Sci.* 1031,127-142 (2004).

Sharma, R.D. and Rukmini C "Rice Bran Oil and Hypocholesterolemia in Rats" *Lipids*, vol. 21, No. 11 (1986) 715-717.

Sierra, S., Lara-Villoslada, F., Olivares, M., Jimenez, J., Boza, J., and Xaus, J. (2005) "Increased immune response in mice consuming rice bran oil" *Eur. J. Nutr.* 44(8):509-516.

Sugano M., and Tsuji E. (1997) "Rice bran oil and cholesterol metabolism". *J. of. Nutrition*, 127(3): 521S-524S.

Sunitha, T. et al., "Lipid Profile of Rats Fed Blends of Rice Bran Oil in Combination with Sunflower and Safflower Oil" *Plant Foods for Human Nutrition* 51: 219-230, 1997.

Suzuki, S. & Oshima, S. (1970) "Influence of blending of edible fats and oils on human serum cholesterol level" *Japanese J. Nutrition* v. 28 (1): Part 1 pp. 3-6; Part 2 pp. 194-198.

Tomeo A.C., Geller M., Watkins T.R. et al., (1995) "Antioxidant Effects of Tocotrienols in Patients with Hyperlipidemia and Carotid Stenosis" *Lipids*, 30:1179-1183.

Watkins T. R., Geller M., Kooenga D. K. and Bierenbaum M. L. (1999) "Hypocholesterolemic and antioxidant effect of rice bran oil nonsaponifiables in hypercholesterolemic subjects" *Environmental and Nutritional Interactions*, 3(2) 115-22.

Xu Z, Hua N., Godber J. S. (2001) "Antioxidant activity of tocopherols, tocotrienols, and gamma oryzanol components from rice bran against cholesterol oxidation accelerated by 2,21-azobis(2-methylpropionamideine) dihydrochloride" *J. Agric.Food.Chem*, 49(4): 2077-2081.

Patent Cooperation Treaty (PCT) International Search Report; International Application No. PCT/US2006/014560, mailed on Jan. 26, 2007.

European Communication Pursuant to Article 94(3) EPC, Dec. 28, 2010, for NATURI LLC., EP App'l No. 06750567.7, filed Nov. 12, 2008.

U.S. Appl. No. 61/366,304, filed Jul. 21, 2010, Nicolosi et al.

PCT Written Opinion of the International Searching Authority, Jan. 26, 2007, for International Application No. PCT/US2006/014560, filed Apr. 13, 2006.

PCT International Search Report, Jan. 26, 2007, for International Application No. PCT/US2006/014560, filed Apr. 13, 2006.

PCT International Preliminary Report on Patentability, Oct. 14, 2008, for International Application No. PCT/US2006/014560, filed Apr. 13, 2006.

U.S. Office Action, Apr. 5, 2010, for U.S. Appl. No. 12/231,318, filed Aug. 29, 2008.

U.S. Office Action, Nov. 9, 2010, for U.S. Appl. No. 12/231,318, filed Aug. 29, 2008.

U.S. Final Office Action, Mar. 23, 2011, for U.S. Appl. No. 12/231,318, filed Aug. 29, 2008.

Rukmini et al., 1991, "Nutritional and Biochemical Aspects of the Hypolipidemic Action of Rice Bran Oil: a review", Journal of the American College of Nutrition, vol. 10(6): 593-601.

* cited by examiner

BIOACTIVE-RICH CONCENTRATES AND NUTRITIVE AND THERAPEUTIC PRODUCTS CONTAINING SAME

FIELD OF THE INVENTION

This invention relates generally to the field of compositions for use as nutraceuticals, food additives or adjuncts to conventional drug therapies. In particular, the invention relates to compositions derived from natural oil sources which can be used for effective and inexpensive prophylaxis of cardiovascular diseases, hypercholesterolemia and/or diabetes, and management of lipid metabolism.

BACKGROUND

Natural phytonutrients, bioactives and antioxidants ("bioactives") are used in the nutraceutical and pharmaceutical industries for their health benefits. For example, polyphenols from grape seed, pine bark and garlic are used in nutraceutical formulations. There are also several potent bioactives present in rice bran and rice germ oil. The unsaponifiable fraction (i.e., the non-fat portion) of rice oil has a high concentration of useful micronutrients and antioxidants such as tocopherols, tocotrienols, γ-oryzanol, phytosterols, polyphenols and squalene, when compared to other vegetable oils. Several clinical studies with rice bran oil (RBO) demonstrated significant hypocholesterolemic, hypolipidemic and anti-atherogenic properties; see, e.g., Table 1.

TABLE 1

Selected RBO clinical studies

| Methodology | Parameters | Reading (mg/dl) | Change (%) | Reference |
|---|---|---|---|---|
| Rice Bran Oil at 60 g/day | Total Cholesterol | 219-177 | −19 | Lichtenstein, A. H, et al. (1994) "Rice Bran oil consumption and plasma lipid levels in moderately hyper cholesterolemic humans." Arteriosclerosis & Thrombosis v. 14 549556 |
| 15 moderately hypercholesterolomic subjects. 32 days, double blind crossover latin square design along with canola, corn and olive oils. | LDL-C | 162-122 | −25 | |
| | HDL-C | no change | no change | |
| | Triglycerides | 131-109 | −17 | |
| Rice Bran Oil at 35 g/day. 12 hypercholesterolemic subjects. 30 days, with a control group of 9 hyper-cholesterolemic subjects with peanut oil. | Total Cholesterol | 247-183 | −25 | Raghuram, T. et al. (1989) "Studies on hypolipidemic effects of dietary Rice Bran Oils in humans." Nutrition Reports International v. 39(5): 889-895 |
| | Triglycerides | 349-212 | −35 | |
| Rice Bran Oil at 60 g/day. 50 healthy females of normal cholesterol. 7 days without blend. 7 days blend with Safflower Oil (SO). At RBO:SO of 70:30 At RBO:SO of 85:15 | Total Cholesterol | 194-164 | −15 | Suzuki, S. & Oshima, S. (1970) "Influence of blending of edible fat and oils on serum cholesterol levels. Japanese J. Nutrition v. 28(1): Part 1 pp. 3-6; Part 2 pp. 194-196. |
| | Total Cholesterol | 164-121 | −26 | |
| | Total Cholesterol | 194-164 | −19 | |

These beneficial properties are attributed to the potent phytonutrients, micronutrients and antioxidants present in the unsaponifiable fraction of the oil (see, e.g., Table 2.) The individual constituents of the rice bran oil unsaponifiable fraction have been well studied for their hypolipidemic, hypoglycemic, hypocholesterolemic, antioxidant and other health benefits in animals and in human subjects.

TABLE 2

Selected study on RBO unsaponifiable fraction

| Methodology | Lipid Parameters | Readings Initial (mg/dl) | Final USF/RBO (mg/dl) | Change % | References |
|---|---|---|---|---|---|
| 0.4% RBO Un-Saponifiable Fraction (USF) vs. equivalent 10% Rice Bran Oil (RBO) studied in rates for hypcholesterolemic effect | Total Cholesterol | 374 | 243/288 | −35/−23 | Sharma, S. D. and Rukmini, C.; Indian J. Med. Res. 1987 Mar; 85: 276-81 |
| | LDL/VLDL | 331 | 195/240 | −41/−27.5 | |
| | HDL | 43 | 48/48 | 11.6/11.6 | |
| Unsaponifiable fraction: 277.7 mg/g γ-oryzanol, 89.99 mg/g phytosterols, 11.66 mg/g tocols, 3.36 mg/g squalene, 0.73 mg/g of octocosanol | Total cholesterol | No change | | | Ha, T., Han, S., Kim, S., Kim, I., Lee, H., and Kim, H., (2005) Nutrition Research 25: 597-606. |
| | Triglycerides | No change | | | |
| | HDL-C | Increase | | | |
| Unsaponifiable fraction | Total cholesterol | Decreased | | | Lee, J., Lee, S., Kim,. M., Rhee, C., Kim, I., and Lee, K (2005) J. Sci. Food. Agri 85: 493-498. |
| | LDL-C | Decreased | | | |
| | Triglycerides | Decreased | | | |
| | HDL-C | No change | | | |

Antioxidant defense mechanisms in biological systems play a major role in the prevention of a number of diseases such as cardiovascular, cerebrovascular, carcinogenic, and other metabolic age-related disorders. Free radicals, such as singlet oxygen, are highly reactive, attack cellular components, can damage DNA, and alter normal metabolism, resulting in a disease state. Humans are under constant challenge by free radicals; unless charged with sufficient antioxidants to quench these free radicals, the pace of damage to the body is increased and can result in various disease states. Antioxidants provide a defense mechanism and help in preventing and arresting the progression of diseases. It is a constant battle to maintain the delicate balance between oxidants and antioxidants in the body. Epidemiological evidence is mounting on the significant role of natural antioxidants and their vital role in maintaining health and preventing diseases.

Cardiovascular disease (CVD) is a leading cause of mortality in the United States and in developed countries around the world. The disease is linked with well-defined risk factors, such as lipid anomalies, arterial hypertension, diabetes, obesity and smoking. The estimated breakdown of the CVD patient population is as follows: High blood pressure: 50.0 million; Coronary heart disease: 13.9 million; Congestive heart failure: 4.7 million; Stroke: 4.0 million; Rheumatic heart disease: 1.8 million.

There is an increasing need to contain this disease effectively without exponentially increasing the associated healthcare costs. Prescription medications alone will not suffice in addressing this need as they have a high direct and indirect cost. Beyond cost, there are also significant side effects associated with prescription drugs and medical practitioners are reluctant to increase dosages unless absolutely needed. For example, statin drugs for lowering cholesterol are effective, but can have undesired side effects.

Rice bran oil (RBO) is obtained from rice bran, i.e., the mesocarp of paddy. RBO is different from other vegetable oils, which are obtained from the seed and/or nuts. Palm oil, coconut oil, olive oil and rice bran oil are obtained from the mesocarp of the fruit. These oils are rich in several natural antioxidants. However, when these oils are processed to an edible grade during normal refining steps, the valuable bioactive micronutrients and antioxidants contained in the unsaponifiable fraction of the oil are degraded or destroyed during normal refining steps, thus reducing both the bioactivity of the micronutrients and antioxidants and their therapeutic benefit. Obtaining a bioactive micronutrient and/or antioxidant-rich rice oil derivate has posed significant challenges to the oil technologist.

Conventional edible oil refining processes yield several by-products, including soap stock, distillate and gums. These by-products contain high concentrations of several of the vegetable oils' unsaponifiable constituents. Although technologies are available for isolating desirable individual constituents and actives, e.g., tocopherols, tocotrienols and γ-oryzanol, etc., in the unsaponifiable fractions of rice bran and other vegetable oils, the art has not advanced far enough in developing therapeutic applications of suitable natural whole food extract concentrates containing such micronutrients, e.g., in the unsaponifiable fraction of vegetable oils.

Although the components of the unsaponifiable fraction of rice bran oil has been reported for its cholesterol reducing property, the dose at which the individual components give the desired effect is very high. Rice bran oil and palm oil is the predominant natural source of tocopherols and tocotrienols (tocols), however, phytosterols are available in several vegetable oils.

γ-oryzanol is unique to rice bran oil among natural products. It occurs in the highest concentration in the bioactives of the unsaponifiable fraction of rice bran oil. γ-oryzanol is a mixture of at least five components. These five components include ferulic acid esters of cycloartenol, 24-methylene cycloartanol, β-sitosterol, 4-methylsterol and methyl ferulate. γ-oryzanol is a potent antioxidant (Joseph Bruno "*The facts on γ-oryzanol*" 1987), demonstrated to have UV-quenching properties, and activity on the hypothalamus, relieving stress by increasing DHEA levels and reducing cortisol levels. In addition, it has been reported to induce fat burning that results in lean body mass. Furthermore, it has been shown to have hypocholesterolemic activity, dissolving aortic streaks (Seetharamiah, G. et al., Atherosclerosis 78: 219-223) and dissolving blood clots. It has also demonstrated beneficial effects on cardiovascular risk factors.

U.S. Pat. No. 5,660,691 discusses isolating tocopherols and tocotrienols from rice distillate. U.S. Pat. No. 5,288,902 discusses isolating γ-oryzanol, another valuable antioxidant, from the soap stock, which is typically discarded as a waste product. However, in these techniques and others, the natural matrix is disrupted, and thus the potency and bioavailability of these components is diminished.

SUMMARY

The present invention provides effective and non-destructive isolation, concentration and use of the bioactive components, in their natural matrix, from the unsaponifiable fraction of rice bran oil or rice germ oil. The importance of the effective isolation and concentration of these bioactives in their natural matrix, has not heretofore been achieved or recognized. Components of the bioactive-rich concentrate acts are believed to act synergistically to produce a more potent and greater hypolipidemic and hypocholesterolemic effect than the art has recognized, e.g., when individual, singly purified bioactives are employed. In accordance with the invention, these natural micronutrients and antioxidants are captured, extracted and concentrated without disrupting or with minimal disruption of the natural matrix within which they exist. Since these micronutrients and antioxidants are in their natural lipid matrix, they are more bioavailable and potent than in their purified isolated form.

One embodiment of the invention features a bioactive-rich concentrate derived from the unsaponifiable fraction of rice germ oil, which includes the unsaponifiable content of rice oil. The concentrate is substantially free of rice bran contaminants and may be substantially free of oil matter such as free fatty acids, fats, and triglycerides, and the unsaponifiable content is present at a concentration 10 to 100 times greater than in raw recovered rice bran oil or rice germ oil. The unsaponifiable contents typically include a 4-dimethyl sterol component, a 4-monomethyl sterol component, a γ-oryzanol component, a polyphenol component, a tocopherol component, and a tocotrienol component.

In an embodiment, the amount of 4-dimethyl sterol component may be about 10-30%, the amount of 4-monomethyl sterol component may be about 4-14%, the amount of γ-oryzanol component may be about 20-40%, the amount of polyphenol fraction component may be about 5-15%, the amount of tocopherol component may be about 5-20%, and the amount of tocotrienol component may be about 5-20%; by weight (based on total weight of the concentrate.)

The bioactive-rich concentrate may be used alone or as part of a formulation, e.g., in combination with a cholesterol lowering drug and/or an HMG CoA reductase inhibitor. Such compositions may be advantageously used for, e.g., lowering serum lipids, cholesterol, blood glucose, triglycerides, and/or HDL-C levels. In formulations or combination therapies, the bioactive-rich concentrate may be present in an amount from about 250 mg to about 1000 mg; the cholesterol lowering drug is present in amount from about 10 mg to about 50 mg, or from about 10 mg to about 100 mg. The HMG CoA reductase inhibitor, e.g., mevastatin, lovastatin, pravastatin, simvastatin, fluvastatin, cerivastatin, atorvastatin, tenivastatin, rosuvastatin, pitavastatin and combinations thereof, is generally present in amount from about 1 mg to about 80 mg. Cholesterol lowering drugs may include bile acid sequestrants such as cholestyramine, colesevelam and colestipol; or fibric acid derivatives such as fenofibrate and gemfibrozil.

Other embodiments of the invention include methods comprising administering the bioactive-rich concentrate, for example, orally, to treating a patient in need thereof suffering from hypertension, hyperlipidemia, obesity, inflammatory disease, arthritis, hypercholesterolemia, cardiovascular disease, cerebrovascular disease, arteriosclerosis, diabetes mellitus, immune dysfunction or cancer, wherein the patient is administered a bioactive-rich concentrate derived from the unsaponifiable fraction of rice germ oil, in a effective dosage regime sufficient to treat the patient.

Thus, the method may comprise treating a patient in need of treatment for total serum cholesterol, LDL-C, apolipoprotein B, triglycerides, improving HDL-C levels, inhibiting platelet aggregation and dissolving aortic streaks, by administering to the patient a bioactive-rich concentrate derived from the unsaponifiable fraction of rice bran oil or rice germ oil, or a composition comprising such a bioactive rich concentrate, in a effective dosage regime sufficient to treat the patient.

Especially useful embodiments of the invention include food products containing a bioactive-rich concentrate derived from the unsaponifiable fraction of rice bran oil or rice germ oil, e.g., breakfast cereals, snack or energy bars, butter substitutes, margarines, salad dressings, mayonnaises, or beverages. Food products of the invention generally contain from about 0.1% to 15% of the bioactive-rich concentrate.

In still another aspect, the invention provides methods for the manufacture of the concentrate disclosed herein comprising thoroughly separating rice germ component solids from remaining solids in rice germ or bran, extracting the oil from the rice germ or bran, and separating the saponifiable from the unsaponifiable components. The latter step may by accomplished by any known method that can produce a micronutrient concentrate in its natural matrix, and preferably is done in the cold immediately after the oil recovery step. The effect is to minimize damage to the micronutrients in the unsaponifiable concentrate otherwise induced by enzymes present in the oil and non germ rice bran components, and greatly to increase the concentration of these micronutrients, while maintaining the microcomponents in their natural chemical state. The concentrate permits the manufacture of convenient dose forms that can be consumed in a pill or capsule to achieve health benefits heretofore obtainable only by consuming much larger quantities of rice bran oil.

DETAILED DESCRIPTION

Definitions

Figure 1:
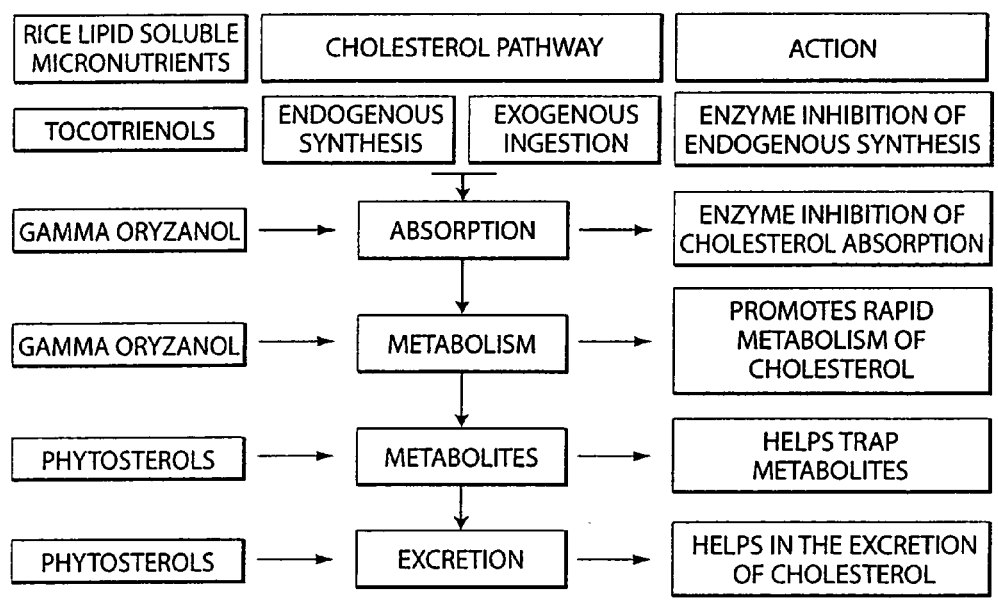
FIG. 1 illustrates the steps in the cholesterol homeostasis pathway.

For convenience, certain terms used in the specification, examples, and appended claims are collected here.

"Phytonutrient" as used herein is includes nonnutritive bioactive plant substance, such as a flavonoids or carotenoids, considered to have a beneficial effect on human health.

"Micronutrients" include phytonutrients, vitamins and minerals which are essential for healthy body function, as well components present in, for example, rice germ oil in very small concentrations that have not been fully characterized but contribute to the known health effects of rice oil preparations.

"Bioactives" collectively include phytonutrients, micronutrients and antioxidants.

"Rice bran contaminants" include all components of rice bran excepting the rice germ component.

"(Natural) matrix" refers to the proportion of naturally-occurring components and the form in which the components are present in rice germ oil. For example, rice oil includes phytosterols that are present naturally as a range of phytosterols of specific chemical structures, and particular esters thereof. "Matrix," in this case, refers to the phytosterol fraction as just described. The natural matrix represents the bioactives occurring in their native form in their natural lipid environment. A key concept of the present invention is that the bioactives, e.g., the micronutrients, in their natural matrix are biologically more potent than their isolated (purified or separately extracted) forms. Conventional techniques used by others to isolate these micronutrients separate them from their lipid substrate and degrade their molecular structure. For example, phytosterols that are present in RBO exist as free sterols as well as sterol esters. They occur in a dissolved state in the natural lipids of RBO. Together, the micronutrient (in its original form) and the lipid in which it exists are termed as the natural matrix. The present invention ensures that the bioactives, e.g., micronutrients, are maintained as they are in their natural lipid environment.

Combination therapy" (or "co-therapy") includes the administration of a bioactive-rich concentrate of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

One embodiment of the invention features a bioactive-rich concentrate derived from the unsaponifiable fraction of rice bran oil or rice germ oil, which includes the unsaponifiable content of rice oil; the concentrate is substantially free of rice bran contaminants; and the unsaponifiable content is present at a concentration 10 to 100 times greater than in rice bran oil or rice germ oil. The unsaponifiable contents include a 4-dimethyl sterol component, a 4-monomethyl sterol component, a γ-oryzanol component, a polyphenol component, a tocopherol component, and a tocotrienol component.

In an embodiment, the amount of 4-dimethyl sterol component may be 10-30%, the amount of 4-monomethyl sterol component may be 4-14%, the amount of γ-oryzanol component may be 20-40%, the amount of polyphenol component may be 5-15%, the amount of tocopherol component may be 5-20%, and the amount of tocotrienol component may be 5-20%; by weight (based on total weight of the concentrate.)

The bioactive-rich concentrate may be used alone or as part of a formulation, e.g., in combination with a cholesterol lowering drug and/or an HMG CoA reductase inhibitor. Such compositions may be advantageously used for, e.g., lowering serum lipids, cholesterol, blood glucose, triglycerides, and/or HDL-C levels. In formulations or combination therapies, the bioactive-rich concentrate may be present in an amount from about 250 mg to about 1000 mg; the cholesterol lowering drug is present in amount from about 250 mg to about 1000 mg. The HMG CoA reductase inhibitor, e.g., mevastatin, lovastatin, pravastatin, simvastatin, fluvastatin, cerivastatin, atorvastatin, tenivastatin, rosuvastatin, pitavastatin and combinations thereof, is generally present in amount from about 1 mg to about 80 mg. Cholesterol lowering drugs may include bile acid sequestrants such as cholestyramine, colesevelam and colestipol; or fibric acid derivatives such as fenofibrate and gemfibrozil.

Other combination compositions contemplated herein include a composition that includes a bioactive-rich concentrate and natural components such as herbs and/or herbal ingredients. Such herbs and/or herbal ingredients may include those used to lower cholesterol levels, such as guggul gum resin derived from or in the form of gum from *Commiphora mukul*, policosanol that may be derived from sugar cane wax, curcumin that may be derived from turmeric, garlic, psyllium, green tea and/or green tea extracts, and licorice and/or licorice extracts. Other combination compositions can include such ingredients as DHA, EPA, CoQ10, fish oil, olive oil, vitamin E and vitamin C.

Especially useful embodiments of the invention include food products containing a bioactive-rich concentrate derived from the unsaponifiable fraction of rice bran oil or rice germ oil. Such food products may include, for example, breakfast cereals, snack or energy bars, butter substitutes, margarines, salad dressings, mayonnaises, or beverages. Food products of the invention generally contain from about 0.1% to about 15% of the bioactive-rich concentrate.

Pure rice germ may be used as one preferred source of oil from which the bioactive-rich concentrates of the invention may be obtained. Rice germ is a by-product of the rice milling industry and may comprise a portion of rice bran. When the lipases present in the germ come into contact with the oil during milling, they can hydrolyze the triglycerides into free fatty acids, which damage the micronutrients. Preferably, the rice germ is polished repeatedly, for example polished with three or four passes or more, and delicately. Hullers should be avoided, and the mills should separate the bran generated from the polishes as well as stringently separate stone and grit from the paddy. Raw rice milling may be more desirable. Rice bran should be separated from the germ after the initial polishing by sieving and air classification, or other density based separation technique, more desirably within 24 hours after polishing, followed by cold storage, e.g., 3-5° C., to stabilize the germ and halt any residual lipase activity.

The germ should be processed as soon as possible after cold storage is initiated. The rice germ oil may be extracted from the germ by cold pressing; solvent extraction, e.g., with non-polar solvents such as hexane, or polar solvents such ethanol or isopropanol; or supercritical fluid extraction techniques, e.g., super critical fluid fractionation, $CO_2$, fluorohydrocarbons, or propane. Such extraction techniques are known by those of skill in the art.

Alternately, the bioactive-rich concentrates of the invention may be obtained from rice bran oil deodorizer distillate (DOD). DOD is obtained as a by-product of the rice bran oil refining industry. Deodorization is the final step of the rice oil refining process; the deodorization step removes the unwanted impurities in crude rice bran oil, such as aldehydes, ketones and sulfur compounds. This process consists of heating the degummed, deacidified, and bleached rice bran oil to about 250° C. under high vacuum and steam injection. During this process, several key micronutrients in rice bran oil such as tocotrienols and tocopherols can be distilled away with the impurities. There is also a significant amount of free fatty acids (FFAs, up to about 60%) in rice bran oil DOD. As such, rice bran oil DOD is less desirable than rice germ oil, but may be used in the invention under controlled conditions. DOD for use in the invention should employ minimal alkali treatment during de-acidification, so that the micronutrients in the oil are preserved. Further, it should be used within a short time, e.g., one week, of its creation, to minimize FFA micronutrient degradation.

The bioactive-rich concentrates of the invention may be produced from crude rice germ oil by, for example any method that would yield the heretofore unobtained high concentration of the components from the unsaponifiable fraction components. Such methods include preferential concentration (selective solubility) using polar solvents such as ethyl alcohol, isopropyl alcohol, etc.; fractionation of the bioactives of the germ oil after converting the FFAs present in the germ oil to methyl esters followed by SCF treatment; and/or FFA conversion to the ethyl or methyl esters using conventional techniques, followed by short path distillation.

These techniques, which are familiar to those in the art, yield a product, which is 5 to 10 times higher in concentration of the key bioactives (e.g., tocotrienols, tocopherols, γ-oryzanol, phytosterols, polyphenols, etc.)

If DOD is used as a raw material, the following techniques may be used to obtain a product with a high concentration of unsaponifiable fraction components: neutralization of FFAs present in the germ oil with sodium bicarbonate, sodium carbonate, sodium hydroxide or calcium hydroxide, followed by filtration of the FFA salts; or converting the FFAs into its (m)ethyl ester, followed by short path distillation or super critical fluid treatment such as super critical fluid fractionation.

These techniques, which are familiar to those in the art, yield the product of the invention, which is about 10, about 20, about 30, about 40 or about 50 to 100 times greater in concentration of certain key micronutrients, such as tocopherols and tocotrienols.

As a reference, the composition of the unsaponifiable content of crude RBO is shown below:

| Constituent | Concentration |
|---|---|
| Total Unsaponifiable Matter | 4.2% |
| 4-dimethyl sterols | 1.8% |
| 4-monomethyl sterols | 0.4% |
| γ-oryzanol | 1.2% |
| Polyphenols and hydrocarbons (squalene, γ-amino butyric acid) | 0.8% |
| Tocopherols | 0.04% |
| Tocotrienols | 0.07% |

Ref: Unilever paper on "Minor constituents of RBO by Deckere and Kover, Nutrition Reviews 54(11) S120-S126

The relative concentration of the phytosterol components of RBO are campasterol: 0.506 (mg/100 g); stigmasterol: 0.271 (mg/100 g); betasitosterol: 0.885 (mg/100 g); other sterols: 0.3 (mg/100 g).

The compositions of the invention (i.e., after processing as described hereinabove) are characterized as follows:

| Constituent | Concentration |
|---|---|
| Total Unsaponifiable Matter | 25-70% |
| 4-dimethyl sterols (phytosterols) | 10-30% |
| 4-monomethyl sterols | 4 to 14% |
| γ-oryzanol | 20 to 40% |
| Polyphenols and hydrocarbons (e.g., squalene, gamma-amino butyric acid) | 5 to 15% |
| Tocopherols (e.g., including α-, β-, γ- and δ-isomers) | 5 to 20% |
| Tocotrienols (e.g., including α-, β-, γ- and δ-isomers) | 5 to 25% |

It should be noted that within each class of micronutrient (tocotrienols, tocopherols, phytosterols, oryzanol, polyphenols), the relative concentration of individual isomers and components is the same as the original source (either rice bran/germ). This "signature" cannot be obtained by mixing isolated purified components.

The bioactive-rich concentrates of the present invention may be produced at an estimated cost of $0.02 to $0.03 per serving, which is several times lower than the individual pharmaceutical compounds targeted at the same ailments. As an example, tocotrienols retail for around $200/kg, and γ-oryzanol retails for around $75/kg.

The preparation of pharmaceutical or pharmacological compositions containing the compositions of matter of the invention will be known to those of skill in the art in light of the present disclosure. Typically, such compositions may be prepared as orally ingestible preparations such as tablets or other solids for oral administration. Alternatively, they may be formulated as injectables, either as liquid solutions or suspensions; solid forms suitable for solution in, or suspension in, liquid prior to injection; as time release capsules; or in any other form currently used, including creams, lotions, mouthwashes, inhalants and the like.

While the compositions of the invention may take many forms, such as capsules, pills and gelcaps, for personal daily or other intermittent use, they also are especially useful when formulated as food additives, e.g. in spreads, frozen desserts, beverages and nutritional bars.

Examples of food products comprising the compositions of the invention include margarines or other spreads of oil based products, bakery products, dairy products, e.g., yogurt, cheese and milk-based drinks, beverages, e.g., soft drinks, fruit juices and tea- and coffee-based drinks, sauces, dressings and mayonnaise and confectionery products, e.g., frozen confectionery products such as water-ice or ice-cream, and dietary supplements such as health bars.

The compounds described herein can be used in compositions comprising fat and non-fat components to provide general health benefits, including cardiovascular benefits, such as lowering cholesterol in the consumer, treating, preventing, and/or inhibiting heart disease (e.g., atherosclerosis, restenosis, thrombosis) and treating other conditions such as hypertension, poor circulation, complications associated with diabetes, cerebrovascular disease, neurological disorders, and liver abnormalities.

The compounds can be used in the production of baked goods in any form, such as mixes, shelf-stable baked goods (including health bars), and frozen baked goods. Applications include cakes, brownies, muffins, bar cookies, health bars, wafers, biscuits, pastries, pies, pie crusts, and cookies, including sandwich cookies and chocolate chip cookies. The baked goods can contain fruit, cream, or other fillings. Other baked good uses include breads and rolls, crackers, pretzels, pancakes, waffles, ice cream cones and cups, yeast-raised baked goods, pizzas and pizza crusts, and other baked salted snacks.

The compositions herein can be used alone or in combination with fats to make shortening and oil products. The fats can be synthetic or derived from animal or vegetable sources, or combinations of these. Shortening and oil products include shortenings, margarines, spreads, butter blends, lards, cooking and frying oils, salad oils, popcorn oils, salad dressings, mayonnaise, and other edible oil products. In a particular embodiment of the present invention, the compositions include margarines, butter, dressings and spreads.

Other uses for the compositions of the present invention include partial or complete replacement fats and/or oils present in peanut butter, frozen desserts such as ice cream and ice cream coatings, whipped toppings, frosting products, processed meat products such as vegetable protein-based meat analog products, sauces, gravies, and dairy products such as milkshakes, milk products, coffee whiteners, and cheese products.

The compounds described herein may also be used in beverage compositions, e.g., dilute water beverages (also called "near-water" beverages), milks, coffees, teas, colas, and fruit juices.

Compositions of the invention may be used as the pharmaceutical, nutraceutical, cosmeceutical and health food dietary supplements for treating health disorders including high blood pressure, hypercholesterolemia, hyperlipidemia, cardiovascular disease, cerebrovascular disease, diabetes, cancer, obesity, inflammatory diseases, arthritis, improve immune function; as a sports and weight loss formulations in improving lean body mass and liver disorders; and other uses including skin care, hair growth, UV protection, antidandruff agents, and cosmeceuticals.

EXEMPLIFICATION

The invention now being generally described, it will be more readily understood by reference to the following examples which are included merely for purposes of illustration of certain aspects and embodiments of the present invention, and are not intended to limit the invention in any way.

Composition A:

Composition A is derived from two starting materials: rice germ and deodorizer distillate. Purified and stabilized rice germ from the bran is obtained from the first two polishes of rice using 2 successive steps. First, size based separation or sieving is conducted. Density based separation (air classification) is then performed. These operations are carried out within 24 Hrs of polishing operation at the mill. These successive steps yield pure rice germ (over 90% purity). This rice germ is maintained in a cold storage facility at 3 to 5 degrees Celsius to arrest the lipase activity and keep it stable. A crude rice germ oil is extracted from this pure rice germ by solvent extraction with hexane. Hexane is then removed to leave behind crude rice germ oil. This crude rice germ oil is then subject to a degumming process, a dewaxing process, and then esterified. This esterified oil is subject to short path distillation and a concentrated fraction of the rich germ oil is collected.

Rice bran oil deodorizer distillate (DOD) is obtained as a by-product of the rice bran oil refining industry. This distillate is subjected to short path distillation and a concentrated fraction is collected.

The two collected fractions from rice germ and DOD are analyzed for their micronutrient content and on the basis of the analysis are combined in proportions to yield Composition A.

Composition A is characterized by HPLC and GC. Within each class of nutrient, the relative concentration of individual isomers and components is the same as the original source (rice bran/germ).

The table below describes a sample preparation of a composition ("Composition A") made in accordance with the invention, and which was tested in an animal study described below:

| Ri-Active ™ Components | g/100 g |
|---|---|
| γ-oryzanol | 30 g/100 g |
| Tocopherols (α, β, γ, d isomers) | 4 g/100 g |
| Tocotrienols (α, β, γ, d isomers) | 7 g/100 g |
| Phytosterols (β-sitosterol, sitosterol, campestrol, stigmasterol and 27 other sterol derivatives | 7 g/100 g |
| Polyphenols (trans ferulic acid, protocatechuic acid, epicatechin, p-coumaric acid, sinapic acid, tricin, a flavonol, GABA and 8 other polyphenols) | 1.0 g/100 g |
| Squalene and other hydrocarbons | Trace amounts |

Hypolipidemia, Hypocholesterolemia and Hypoglycemia Study in Syrian Hamsters

This study was undertaken to evaluate the efficacy and safety of a composition of the invention noted above. Syrian golden hamsters (60) were fed semi-purified diets containing coconut oil and 0.5% cholesterol to induce moderate hypercholesterolemia and divided into 6 groups of 10 animals each. Group 1 (Placebo) continued to be fed the same control diet. Group 2 (Positive control) was fed 0.1% phytosterols in the control diet (FDA approved natural hypocholesterolemic agent) Group 3 was fed 0.5% phytosterols in the control diet, Group 4 was fed 0.1% Ri-Active™ in the control diet, Group 5 was fed 0.5% Ri-Active™ in the control diet, and Group 6 was fed 1% Composition A in the control diet. All diets were prepared by the Research Diets, Pennsylvania USA. All animals were fed the corresponding diets for 9 weeks. Weekly body weights were monitored. Physical symptoms, if any and gastrointestinal function were also monitored in all the animals. Blood was drawn by retro orbital sinus at the end of 4, 6 and 9 weeks, from each animal and analyzed for total cholesterol, LDL-C, Triglycerides, HDL-C, serum glucose levels AST and ALT.

Table 3 shows results of the Watson clinical study, investigating the effects of RBO performed using a RBO unsaponifiable fraction, using rice bran oil as a whole. This study was conducted on 50 human subjects over a 12 month period showed that administering 3.1 g/day of RBO unsaponifiables resulted in a 14.1% reduction in total cholesterol and a 20.5% reduction in LDL-C in addition to an increase in HDL-C levels and significant decrease in triglycerides levels

TABLE 3

| Effect of RBO unsaponifiable fraction in hypercholesterolemic subjects | | | |
|---|---|---|---|
| Methodology | Lipid Parameters | Reduction/Increase | Reference |
| 50 hypercholesterolemic subjects received in random blinded fashion 3.1 g of RBO non-saponifiables or placebo for 12 months | Total Cholesterol LDL-Cholesterol HDL-C/Total Cholesterol Triglycerides/HDL-C | −14.1% (p < 0.05) −20.6% (p < 0.05) +41.17% (p < 0.025) −43.98% (p < 0.05) | T. R. Watkin, M. Geller, D. K. Kooyenga and M. L. Bierenbaum; Environmental and Nutritional Interactions, 13: 115-122, 1999 |

The current studies were undertaken at least in part to investigate if Composition A, with ten times the concentration of that used in Watkin's study, and having multiple bioactives from the RBO unsaponifiable fraction would act synergistically resulting in the overall cardiovascular risk benefits and would lower LDL cholesterol to an even greater extent while increasing the HDL-C levels.

Test Results: (Comparison Between Groups)

The results indicated significant hypocholesterolemic, hypolipidemic and hypoglycemic effect of Composition A compared to two groups: 1) phytosterols, which is the positive control or "gold standard", and are currently the only natural products in the market with a FDA health claim for cardiovascular health (at least 800 mg of phytosterols or 1300 mg of phytosterol esters in two meals per day); and 2) a placebo control (no treatment) group. Phytosterols may compete with cholesterol uptake releasing cholesterol for excretion. The average decline in LDL-c levels through the use of phytosterols is thought to be between 8%-15% in humans.

Figure 2:
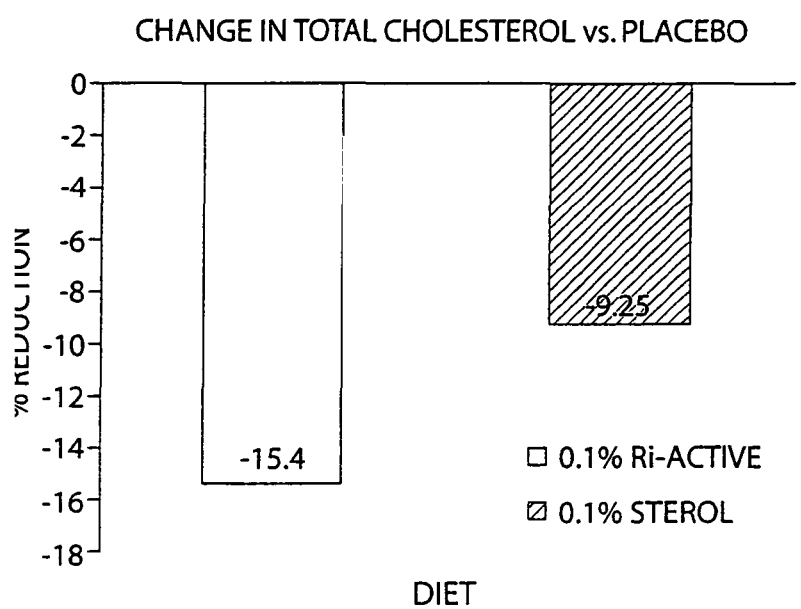
FIG. 2 illustrates the performance of a bioactive-rich concentrate of the invention as compared to a placebo high cholesterol diet. The comparison is based on a measure of total cholesterol reduction in hamsters after 9 weeks of administering the treatment.

0.1% Composition A (~10 mg Dosage):

In the 0.1% Composition A group, total cholesterol levels were 16% lower (242 mg/dl) and statistically significant (P<0.008) when compared to placebo group (287 mg/dl) and more than 6% greater reduction than the 0.1% phytosterols group (260 mg/dl). The significance of this result is further underscored because the 0.1% Composition A group contains less than 1/10th the concentration of phytosterols as compared to the 0.1% phytosterol group. FIG. 2 shows a comparative performance of Composition A as measured by total cholesterol reduction.

Figure 3:
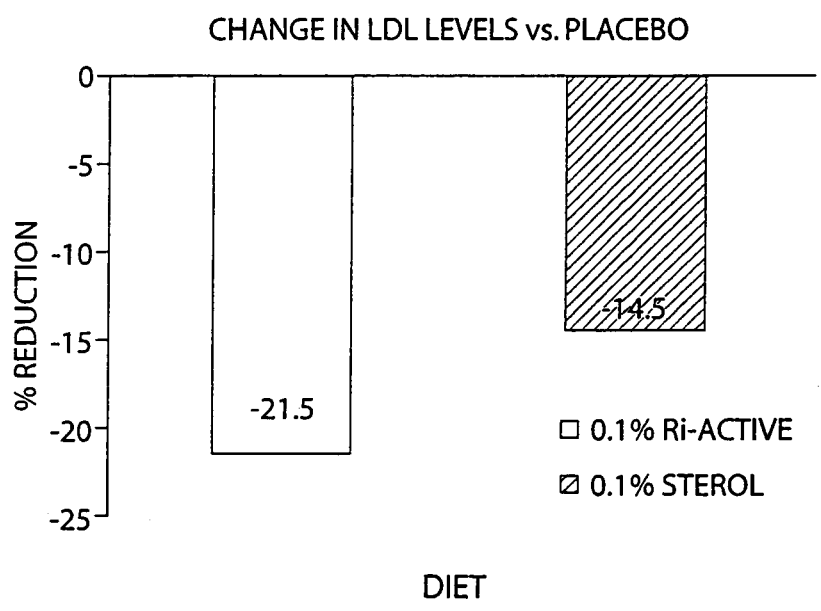
FIG. 3 illustrates the performance of a bioactive-rich concentrate of the invention as compared to a placebo high cholesterol diet. The comparison is based on a measure of LDL-cholesterol reduction in hamsters after 9 weeks of administering the treatment.

The decrease in LDL-C in this group (135 mg/dl) was remarkable and significant (P<0.001) with 22% reduction when compared to placebo group (171 mg/dl) and nearly 8% greater reduction when compared with 0.1% phytosterol group (146 mg/dl) as seen in FIG. 3.

Triglycerides also showed an excellent reduction of 21% (242 mg/dl) when compared with placebo (306 mg/dl) and this was 12% greater to reduction shown by the 0.1% phytosterol group (279 mg/dl).

Figure 4:
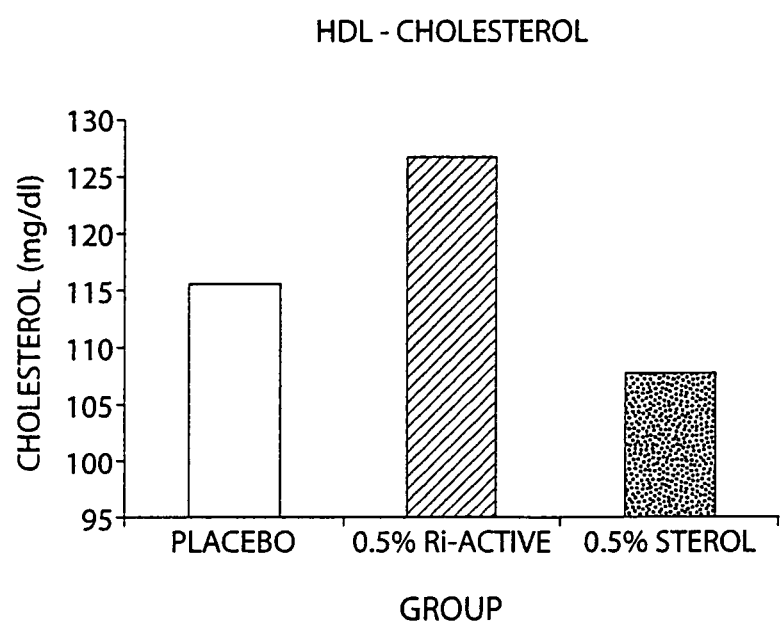
FIG. 4 illustrates the performance of a bioactive-rich concentrate of the invention as compared to a placebo high cholesterol diet. The comparison is based on a measure of HDL-cholesterol in mg/dL in hamsters after 9 weeks of administering the treatment.

0.5% Composition A (~50 mg Dosage):

Increasing Composition A dosage by 5 times showed a significant increase in HDL-C levels. HDL-C levels in this group (127 mg/dl) increased by 10% more than the placebo group (115 mg/dl) and 17.6% more than the 0.5% phytosterol group (108 mg/dl). These results were statistically significant with P<0.022 (FIG. 4). This indicates a natural product that demonstrates an increase in HDL-C along with a significant decrease in LDL-C. This finding may be supported by previously published human clinical studies conducted over a 12-month period with RBO unsaponifiable fraction (Watkins et al. in 1990: Table 3). The phytosterol groups showed a reduction in HDL-C levels as predicted by previous studies.

Figure 5:
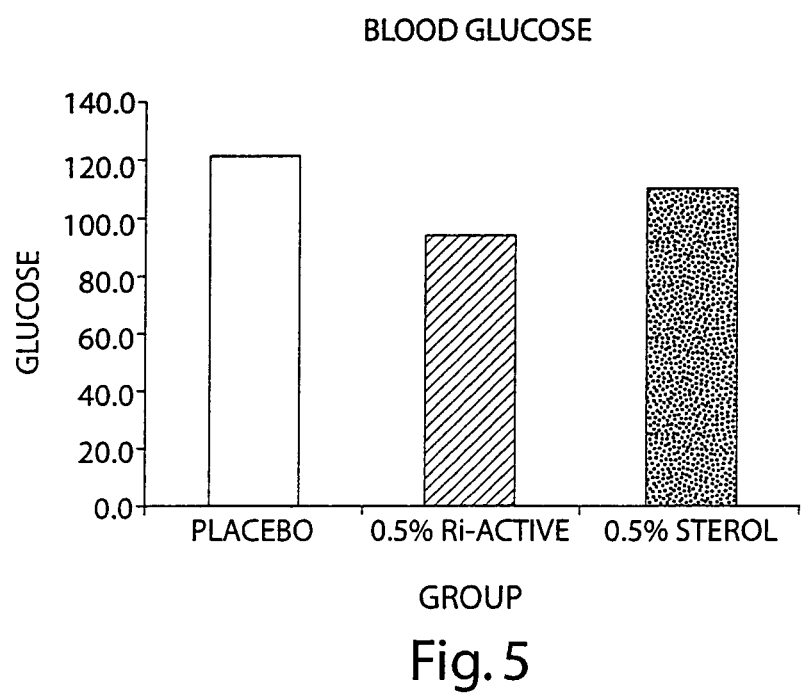
FIG. 5 illustrates the performance of a bioactive-rich concentrate of the invention as compared to a placebo high cholesterol diet. The comparison is based on a measure of blood glucose levels in hamsters after 9 weeks of administering the treatment.

Increasing Composition A dosage by 5 times also showed significant hypoglycemic effect (P<0.015) by lowering blood glucose levels to 93 mg/dl which was 23% lower compared to the placebo diet (121 mg/dl) and 15.6% reduction compared to the 0.5% phytosterol treatment group (111 mg/dl). These results were statistically significant with P<0.030 (See FIG. 5).

Increasing the phytosterol dosage by 5 times (0.5% phytosterol group) did not show any statistically significant reduction in either total cholesterol or LDL-C as compared to the 0.1% Composition A group (0.1% Composition A group had 1/50th the concentration of phytosterols as compared to the 0.5% phytosterol group). Further, there was no statistical significance in the total cholesterol, LDL-C and Triglycerides reduction between the 0.5% phytosterol group and 0.5% Composition A groups.

Animals as their Own Control:

The group comparisons above indicate a statistically significant improvement in lipid parameters for the 0.1% Composition A group, the 0.5% Composition A group and the 0.5% phytosterol group (0.5% phytosterol group is superior to 0.1% phytosterol group as predicted by prior studies).

TABLE 6

Lipid parameters of Placebo group

| Parameter | Peak (Week 4) | Final (Week 9) | Change (%) |
|---|---|---|---|
| Total Cholesterol | 396 ± 87 | 287 ± 26 | −27.5 |
| LDL-C | 272 ± 77 | 171 ± 18 | −37.1 |
| HDL-C | 124 ± 30 | 115 ± 15 | −7.2 |
| Triglycerides | 470 ± 220 | 306 ± 111 | −34.9 |
| Glucose | 125 ± 28 | 121 ± 15 | −3.2 |

TABLE 7

Lipid parameters of 0.1% Ri-Active

| Parameter | Peak (Week 4) | Final (Week 9) | Change (%) |
|---|---|---|---|
| Total Cholesterol | 381 ± 141 | 243 ± 36 | −36.2 |
| LDL-C | 271 ± 166 | 135 ± 21 | −50.1 |
| HDL-C | 110 ± 20 | 108 ± 20 | N.C. |
| Triglycerides | 379 ± 286 | 242 ± 69 | −36.1 |
| Glucose | 126 ± 67 | 110 ± 17 | −12.8 |

TABLE 8

Lipid parameters of 0.5% Ri-Active

| Parameter | Peak (Week 4) | Final (Week 9) | Change (%) |
|---|---|---|---|
| Total Cholesterol | 436 ± 126 | 279 ± 61 | −36 |
| LDL-C | 322 ± 109 | 153 ± 41 | −52.4 |
| HDL-C | 115 ± 24 | 127 ± 21 | 10.3 |
| Triglycerides | 532 ± 224 | 291 ± 148 | −54.7 |
| Glucose | 121 ± 42 | 93 ± 8 | −22.7 |

TABLE 9

Lipid parameters of 0.5% Phytosterols group

| Parameter | Peak (Week 4) | Final (Week 9) | Change (%) |
|---|---|---|---|
| Total Cholesterol | 340 ± 143 | 279 ± 26 | −18 |
| LDL-C | 233 ± 134 | 134 ± 18 | −42.5 |
| HDL-C | 108 ± 16 | 108 ± 11 | N.C. |
| Triglycerides | 440 ± 346 | 259 ± 126 | −41.1 |
| Glucose | 122 ± 47 | 111 ± 21 | −9.5 |

TABLE 10

Ratio Comparison of Treatment Groups

| | TC/HDL-C | | LDL-C/HDL-C | |
|---|---|---|---|---|
| Treatment | Initial | Final | Initial | Final |
| Placebo | 3.28 | 2.51 | 2.28 | 1.51 |
| 0.1% Ri-Active | 3.40 | 2.25 | 2.45 | 1.25 |
| 0.5% Ri-Active | 3.78 | 2.19 | 2.79 | 1.20 |
| 0.5% Phytosterols | 3.15 | 2.58 | 2.16 | 1.34 |

Safety

Composition A showed good animal growth performance and health maintenance at very high doses. It did not show any adverse effects or any physical signs and symptoms of toxicity. Further, the AST and ALT measurement made by increasing the Composition A dosage by 10 times (1% Composition A) were not different from the control group and indicated its safety.

Observations

1. Composition A at 0.1% (10 mg Composition A in the diet) contains 1.1 mg Tocos (Tocopherol and Tocotrienols), 3.0 mg Gamma Oryzanol and less than 1.0 mg of phytosterols. In the light of these low bioactive concentrations, the observed significant hypolipidemic effect in 0.1% Composition A group is significant. It shows the synergistic effect of RBO bioactives acting in concert at very low concentration in their natural matrix. Previous studies on individually purified RBO bioactives have never shown any hypocholesterolemic or hypolipidemic at such low concentrations.

2. Composition A at 5 times the concentration (0.5%) demonstrated a significant increase in HDL-C, which is a positive factor to reduce the risk of CVD.

3. Composition A at 5 times the concentration (0.5%) demonstrated a significant hypoglycemic effect, which is again risk factor of cardiovascular disease.

4. This study demonstrates that Composition A is safe and superior to plant phytosterols (the gold standard) for the reduction of CVD risk factors. These results indicate significant hypocholerolemic, hypolipidemic and hypoglycemic effect of 0.1% Composition A compared with 0.1% phytosterols which may be a "gold" standard, as well as compared with placebos. Total cholesterol levels were lower and statistically significant (P value between groups is 0.010). It has shown a reduction of 16% compared to placebo; and more than 6% reduction compared to phytosterols @ 1/10th the sterol concentration, which is statistically significant (P value between groups less than 0.001). The decrease in LDL-C was 22% when compared with placebo; and nearly 8% decrease when compared with 0.1% phytosterols @ 1/10th the sterol concentration. Increasing Composition A dosage by 5 times (0.5% Composition A group) showed a significant increase of HDL-C levels by 10% over the placebo (high cholesterol diet) group. This natural product demonstrates an increase in HDL-C, which is a well-recognized positive factor in controlling CVD. Increasing Composition A dosage by 5 times (0.5% Composition A group) also showed significant hypoglycemic effects by lowering blood glucose levels by 23% over the placebo group. Composition A showed good growth performance and did not show any adverse effects by any signs and symptoms or by the AST and ALT measurement which were not different from the control group indicating its safety.

The Results Shown in the Above Examples Suggest that:

1. 0.1% Composition A (10 mg of Composition A in the diet) includes 1.1 mg Tocos, 3.0 mg Gamma Oryzanol and less than 1.0 mg of phytosterols. The observed results show a significant synergistic effect of RBO bioactives acting in concert at very low concentration in their natural matrix.

2. Composition A at 5 times the concentration (of 0.1%,), demonstrate significant raise in HDL-C, which is a positive factor to reduce the risk of CVD.

3. Composition A at 5 times the concentration (of 0.1%) demonstrated significant hypoglycemic effect, which is a factor to reduce the risk of cardiovascular disease.

4. Composition A at 5 times the concentration (of 0.1%), demonstrate significant raise in HDL-C, which is a positive factor to reduce the risk of CVD.

5. Composition A at 5 times the concentration (of 0.1%) demonstrated significant hypoglycemic effect, which is again a factor to reduce the risk of cardiovascular disease.

6. Composition A demonstrated to be safe without any adverse effects and more efficacious than a "gold" standard, phytosterol.

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

Also incorporated by reference are the following: Nicolosi R. J., Ausman L. M., and Hegstead M. (1991) "Rice bran oil lowers serum and LDL lipoprotein cholesterol and apo-B levels in non-human primates" *Atherosclerosis.* 88(2-3) 133-142; Rukmini C., and Raghuram T. C., (1991) "Nutritional and biochemical aspects of the hypolipidemic action of rice bran oil: A review" *J. Amer. Coll. Nutrition.* 10: 366-375; Sugano M., and Tsuji E., (1997) "Rice bran oil and cholesterol metabolism". J. of. Nutrition, 127(3): 521S-524S; Qureshi A. A., Qureshi N., Hasler-Rapacz J. O., (1991) "Dietary tocotrienols reduce concentrations of plasma cholesterol, apolipoprotein B, thromboxane B2 and platelet factor 4 in pigs with inherited hyperlipidemias." *Am. J. Clin. Nutr.* 53:1021S; Qureshi A. A., Bradlow B. A., Salser W. A., Brace L. D., (1997), "Novel tocotrienols of rice bran modulate cardiovascular disease risk parameters of hypercholesterolemic humans," J. Nutr. Biochem 8: 1-9; Nesaratnam K., Stephen R., Dils R., Darbre P., (1998) "Tocotrienols inhibit the growth of breast cancer cells irrespective of estrogen receptor status." *Lipids,* 33(5): 461-469; Tomeo A. C., Geller M., Watkins T. R., (1995) "Antioxidant effects of tocotrienols in patients with hyperlipidemia and carotid stress." *Lipids,* 30:1179; Xu Z, Hua N., Godber J. S., (2001), "Antioxidant activity of tocopherols, tocotrienols, and gamma oryzanol components from rice bran against cholesterol oxidation accelerated by 2,21-azobis(2-methylpropionamideine)dihydrochloride." J. Agric. Food. Chem, 49(4): 2077-81.; Ando Y., Pharcos I., (1984) "Effect of gamma oryzanol as sunscreen agent", Jpn. J. Cosmetic Sci. Soc, (1) 41; Akihisa T., Yasukawa K., Yamaura M., Ukiya M., Kimura Y., Shimizu N., and Arai K., (2000) "Triterpene alcohol and sterol ferulates from rice bran and their antiinflammatory effects", J. Agri. Food. Chem, 48:2313-2319; Ieiri T., Kase N., Hashigami Y., Nakumura T., Shimoda S., (1982) "Effect of gamma oryzanol on the hypothalamo-pituitary axis in the rat", *Nippon Naibunpi Gokkai Zasshi* 58(10): 1350-6; Bouic P. J. D., Etsbeth S., Liebenberg R. W., Albrecht C. F, Pegel G., Van Jaarsveld P. P., (1996) "Beta-sitosterol and beta-sitosterol glucoside stimulate human peripheral blood lymphocyte proliferation: Implication for their use as an immunomodulatory vitamin combination", International. J. Immunopharmacology, 18(12): 693-700; Ann Hudson, Dinh P. A., Kokubun T., Simmonds S. J., and Gescher A., (2000) "Characterization of potentially chemopreventive phenols in extracts of brown rice that inhibit the growth of human breast and colon cancer cells". Cancer Epidemiology, Biomarkers & Prevention. 9:

1163-1170; Sunita T. Manorama R., and Rukmini C. (1996) "Lipid profile on blended oils with rice bran oil—A study in human subjects". Report to Dabur India Ltd. Asia Pacific Journal of Clinical Nutrition; Sunita T., Manorama R. and Rukmini, C. (1997) "Lipid profile of rats fed a blend of rice bran oil in combination of safflower/sunflower oil." Plant Foods for Human Nutrition 51: 219-230; Reddy Sastry C. V., Rukmini C., Ike Lynch, and McPeak D., (1999) "Process for obtaining micronutrient enriched rice bran oil." U.S. Pat. No. 5,985,344; Rukmini C., (2000) In "Phytochemicals as Bioactive Agents." Bidlack, W. R., Omaye, S. T., Meskin, M. S., Topham, D. K. W (Ed), Chapter 13 "Bioactives in Rice Bran and Rice Bran Oil." 213-239; Rukmini C., Reddy Sastry C., McPeak P., and Lynch I. (2000) "Method for treating hypercholesterolemia, hyperlipidemia, and atherosclerosis." U.S. Pat. No. 6,126,943; Patricia McPeak, Rukmini C., Reddy Sastry Cherukuri (2001), "Supportive therapy for Diabetes, Hyperglycemia and Hypoglycemia" U.S. Pat. No. 6,303,586; Rukmini C., Reddy Sastry C. V., McPeak P., and Lynch I. (2002) "Method for treating hypercholesterolemia, hyperlipidemia, and atherosclerosis." U.S. Pat. No. 6,350,473; Rukmini C. (2003) Phytochemical Products: rice bran; Chapter 17, Pg 347-376; in "Phytochemical Functional Foods" (Ed) Ian Johnson and Gary Williamson (CRC) Woodhead Publishing Ltd. (Great Briton); Rukmini C., Patricia McPeak, Reddy Sastry V. Cherukuri, Ike Lynch and Qureshi A. (2003) "Method for treating hypercholesterolemia, hyperlipidemia, and atherosclerosis." U.S. Pat. No. 6,558,714; Rukmini C., Patricia McPeak, Reddy Sastry Cherukuri, Ike Lynch and Qureshi A., (2004) "Method for treating hypercholesterolemia, hyperlipidemia, and atherosclerosis." U.S. Pat. No. 6,733,799; Watkins T. R., Geller M., Kooenga D. K. and Bierenbaum M. L. (1999) "Hypocholesterolemic and antioxidant effect of rice bran oil unsaponifiables in hypercholesterolemic subjects" Environmental and Nutritional Interactions, 3(2) 115-22; Lee, J., Lee, S., Kim, M., Rhee, C., Kim, I., and Lee, K (2005) "Beneficial effect of the unsaponifiable matter from rice bran on oxidative stress in vitro compared t with alpha tocopherol." J. Sci. Food. Agri 85: 493-498.; Ha, T., Han, S., Kim, S., Kim, I., Lee, H., and Kim, H., (2005) "Bioactive components in rice bran oil improve lipid profile in rats fed a high-cholesterol diet" Nutrition Research 25: 597-606; Cicero, A. F., and Gaddi, A., (2001) "Rice bran oil and gamma oryzanol in the treatment Hyperlipoprotenaemias and other conditions" Phytotherapy. Res, 15-277-289; Raghuram, T. C., Brahmaji Rao, U., and Rukmini, C., (1989), "Studies on the Hypolipidemic Effects of Dietary Rice Bran Oil in Human Subjects". Nutrition Reports. International 39:889-895; Hegsted, M., Kousik, C. S., (1994) "*Rice Bran and Rice Bran Oil may lower heart disease risk by decreasing cholesterol synthesis in the body*. Louisiana Agriculture. 37(2): 16-17; Cicero, A. F., and Gaddi, A., (2001) "Rice bran oil and gamma oryzanol in the treatment Hyperlipoprotenaemias and other conditions" Phytotherapy. Res, 15-277-289; Rong, N., Ausman, L. M., Nicolosi, R. J., (1997) "Gamma-oryzanol decreases cholesterol absorption and aortic streaks in hamsters." Lipids 32(3): 303-309; Seetharamiah, G., and Chandrasekhara, N., (1989) "Studies on Hypocholesterolemic Activity of Rice Bran Oil" Atherosclerosis. 78: 219-223; Sarma, R. D., & Rukmini, C., (1986) "Rice bran oil and hypocholesterolemia in rats" Lipids, 21:715-717; Sarma, R. D, Rukmini, C., (1987), "Hypocholesterolemic activity of the unsaponifiable matter of rice bran oil"., Ind J. Med. Res., 85: 278-81; Rukmini, C.,(1988) "*Chemical, Nutritional and Toxicological studies of rice bran oil*." Food Chemistry., 30: 257-268.; Sierra, S., Lara-Villoslada, F., Olivares, M., Jimenez, J., Boza, J., and Xaus, J. (2005) "*Increased immune response in mice consuming rice bran oil*" Eur. J. Nutr. 554: 1-8; Minhajuddin, M., Beg, Z. H. and Iqbal, J. (2005) "*Hypolipidemic and antioxidant properties of tocotrienol rich fraction isolated from rice bran oil in experimentally induced hyperlipidemic rats*." Food and Chemical Toxicology 43: 747-753.

Commonly-owned patent application U.S. Ser. No. 11/251,875, which claims priority to provisional patent application No. 60/619,879 filed Oct. 18, 2004 are both hereby incorporated by reference.

What is claimed is:

1. A composition comprising a bioactive-rich concentrate derived from rice bran oil/rice germ oil following a physical process, comprising
    an unsaponifiable content in an amount from 25-70% by weight;
    wherein the unsaponifiable content comprises
    γ-oryzanol in an amount from 20-40% by weight of the concentrate; tocopherols from 5-20% by weight of the concentrate; and tocotrienols from 5-25% by weight of the concentrate.

2. The composition of claim 1, wherein the unsaponifiable content further comprises 4-dimethyl sterol components, 4-monomethyl sterol components, and polyphenols.

3. The composition of claim 2, wherein the 4-dimethyl sterol component is 10-30% by weight; the 4-monomethyl sterol component is 4-14% by weight; and the polyphenol component is 5-15% by weight.

4. A food product comprising the composition of claim 1 and a food substance.

5. The food product of claim 4, wherein the food product is a breakfast cereal.

6. The food product of claim 4, wherein the food product is a snack or energy bar.

7. The food product of claim 4, wherein the food product is a butter substitute, margarine, salad dressing, mayonnaise, or beverage.

8. The food product of claim 4, wherein the composition comprises from about 0.1% to 15% by weight of the food product.

9. A pharmaceutical dosage form comprising the composition of claim 1 in a capsule, pill, or gelcap.

10. A pharmaceutical dosage form comprising the composition of claim 1, containing from about 250 mg to about 1000 mg of the composition.

11. The composition of claim 1, additionally comprising a second agent selected from a cholesterol lowering drug and an HMG CoA reductase inhibitor.

12. The composition of claim 11, wherein the second agent is an HMG CoA reductase inhibitor selected from the group consisting of mevastatin, lovastatin, pravastatin, simvastatin, fluvastatin, cerivastatin, atorvastatin, tenivastatin, rosuvastatin, pitavastatin and combinations thereof.

13. The composition of claim 11, wherein the second agent is a cholesterol lowering drug selected from a bile acid sequestrant selected from the group consisting of cholestyramine, colesevelam, and colestipol or a fibric acid selected from the group consisting of fenofibrate and gemfibrozil.

14. The composition of claim 1, additionally comprising DHA, EPA, and/or fish oil.

15. A method of treating a patient in need of lowering serum lipids, cholesterol, blood glucose, and/or triglycerides, comprising administering to the patient an effective amount of the composition of claim 1.

16. A method of increasing HDL-Cholesterol levels in a patient comprising administering to the patient the composition of claim 1 in an amount sufficient to increase the patient's HDL-Cholesterol levels.

17. A method of decreasing LDL-Cholesterol levels in a patient comprising administering to the patient the composition of claim 1 in an amount sufficient to decrease the patient's LDL-Cholesterol levels.

18. A method of decreasing triglyceride levels in a patient comprising administering to the patient the composition of claim 1 in an amount sufficient to decrease the patient's triglyceride levels.

19. A method of treating hyperlipidemia, cardiovascular disease, cerebrovascular disease, arteriosclerosis, or diabetes mellitus in a patient in need of such treatment, comprising administering a composition of claim 1 to the patient.

* * * * *